United States Patent
Medoro et al.

(10) Patent No.: US 9,310,287 B2
(45) Date of Patent: Apr. 12, 2016

(54) METHOD AND APPARATUS FOR THE IDENTIFICATION AND HANDLING OF PARTICLES

(75) Inventors: Gianni Medoro, Casalecchio di Reno (IT); Nicoló Manaresi, Bologna (IT); Stefano Gianni, Ravenna (IT)

(73) Assignee: SILICON BIOSYSTEMS S.P.A., Bologna (IT)

( * ) Notice: Subject to any disclaimer, the term of this patent is extended or adjusted under 35 U.S.C. 154(b) by 1082 days.

(21) Appl. No.: 12/740,170

(22) PCT Filed: Oct. 28, 2008

(86) PCT No.: PCT/IB2008/002873
§ 371 (c)(1),
(2), (4) Date: Sep. 10, 2010

(87) PCT Pub. No.: WO2009/056941
PCT Pub. Date: May 7, 2009

(65) Prior Publication Data
US 2010/0331205 A1 Dec. 30, 2010

(30) Foreign Application Priority Data
Oct. 29, 2007 (IT) .............................. TO2007A0771

(51) Int. Cl.
*G06F 19/10* (2011.01)
*G01N 15/14* (2006.01)

(52) U.S. Cl.
CPC ............ *G01N 15/14* (2013.01); *G01N 15/1475* (2013.01); *G01N 15/1484* (2013.01); *G01N 2015/149* (2013.01); *G01N 2015/1477* (2013.01)

(58) Field of Classification Search
None
See application file for complete search history.

(56) References Cited

U.S. PATENT DOCUMENTS

| | | | |
|---|---|---|---|
| 5,252,493 A | 10/1993 | Fujiwara et al. |
| 5,279,493 A | 1/1994 | Halder |
| 5,888,370 A | 3/1999 | Becker et al. |
| 5,945,281 A | 8/1999 | Prabhu |
| 6,149,789 A | 11/2000 | Benecke et al. |
| 6,203,683 B1 | 3/2001 | Austin et al. |
| 6,264,815 B1 | 7/2001 | Pethig et al. |
| 6,294,063 B1 | 9/2001 | Becker et al. |
| 6,824,664 B1 | 11/2004 | Austin et al. |
| 6,830,729 B1 | 12/2004 | Holl et al. |
| 6,875,329 B2 | 4/2005 | Washizu et al. |
| 6,888,721 B1 | 5/2005 | Moghaddam et al. |
| 6,911,132 B2 | 6/2005 | Pamula et al. |
| 6,977,033 B2 | 12/2005 | Becker et al. |
| 7,147,763 B2 | 12/2006 | Elrod et al. |
| 7,250,933 B2 | 7/2007 | De Boer et al. |
| 7,307,328 B2 | 12/2007 | Meyer et al. |
| 7,488,406 B2 | 2/2009 | Hughes et al. |
| 7,641,779 B2 | 1/2010 | Becker et al. |
| 8,216,513 B2 | 7/2012 | Becker et al. |
| 8,349,160 B2 | 1/2013 | Medoro et al. |
| 8,388,823 B2 | 3/2013 | Manaresi et al. |
| 2002/0031838 A1 | 3/2002 | Meinhart et al. |
| 2002/0036139 A1 | 3/2002 | Becker et al. |
| 2002/0070114 A1 | 6/2002 | Miles |
| 2002/0125138 A1 | 9/2002 | Medoro |
| 2002/0132316 A1 | 9/2002 | Wang et al. |
| 2003/0044832 A1 | 3/2003 | Blankenstein |
| 2003/0047456 A1 | 3/2003 | Medoro |
| 2003/0073110 A1 | 4/2003 | Aritomi et al. |
| 2004/0011652 A1 | 1/2004 | Bressler |
| 2004/0055891 A1 | 3/2004 | Pamula et al. |
| 2004/0058450 A1 | 3/2004 | Pamula et al. |
| 2004/0063196 A1 | 4/2004 | Muller et al. |
| 2004/0159546 A1 | 8/2004 | Zhang et al. |
| 2004/0191789 A1 | 9/2004 | Manaresi et al. |
| 2004/0209354 A1 | 10/2004 | Mathies et al. |
| 2004/0229210 A1 | 11/2004 | Sabry et al. |
| 2005/0014146 A1 | 1/2005 | Manaresi et al. |
| 2005/0112541 A1 | 5/2005 | Durack et al. |

(Continued)

FOREIGN PATENT DOCUMENTS

| | | |
|---|---|---|
| DE | 3931851 | 4/1992 |
| DE | 10203636 | 2/2004 |
| DE | 19500660 | 12/2007 |
| EP | 0 500 727 A1 | 9/1992 |
| EP | 1145766 | 8/2007 |
| EP | 1304388 | 2/2008 |
| EP | 1179585 | 7/2008 |
| JP | 58211272 | 12/1983 |
| JP | 2002311461 A | 10/2002 |
| JP | 2002536167 A | 10/2002 |
| JP | 2003121886 A | 4/2003 |
| JP | 2003202604 A | 7/2003 |

(Continued)

OTHER PUBLICATIONS

Long et al. (IEEE Transactions on Information Technology in Biomedicine, 2005, 9:407-412).*

(Continued)

*Primary Examiner* — Lori A Clow
*Assistant Examiner* — Olivia Wise
(74) *Attorney, Agent, or Firm* — Marshall, Gerstein & Borun LLP

(57) ABSTRACT

Disclosed herein are methods and equipment for the optimized selection and isolation, within a respective population, of elements of interest and/or utility for a series of subsequent operations, which can include the phases of: a) identifying, for each particle, at least one of a plurality of characteristic parameters; b) selecting the particles of interest, comparing for each of these the at least one parameter with a respective reference parameter; c) storing, for each of the particles, the at least one parameter identified; d) processing the value of a function of the stored parameter, associating the function with a criterion for selection of the particles of interest chosen from a group of possible selection criteria; e) establishing for each particle a threshold criterion to be used as reference parameter, on a time by time basis according to the result of the processing.

17 Claims, 8 Drawing Sheets

(56) References Cited

U.S. PATENT DOCUMENTS

| | | | |
|---|---|---|---|
| 2005/0214736 A1 | 9/2005 | Childers et al. | |
| 2006/0051775 A1 | 3/2006 | Bianchi | |
| 2006/0072804 A1* | 4/2006 | Watson et al. | 382/133 |
| 2006/0086309 A1 | 4/2006 | Manger et al. | |
| 2006/0139638 A1 | 6/2006 | Muller et al. | |
| 2006/0177815 A1 | 8/2006 | Soh et al. | |
| 2006/0223178 A1 | 10/2006 | Barber et al. | |
| 2006/0228749 A1 | 10/2006 | Wang et al. | |
| 2007/0026413 A1 | 2/2007 | Toner et al. | |
| 2007/0026415 A1 | 2/2007 | Fuchs et al. | |
| 2007/0051412 A1 | 3/2007 | Heath et al. | |
| 2007/0059683 A1 | 3/2007 | Barber et al. | |
| 2007/0172903 A1 | 7/2007 | Toner et al. | |
| 2007/0195324 A1 | 8/2007 | Adams et al. | |
| 2007/0250301 A1 | 10/2007 | Vaisberg et al. | |
| 2008/0058991 A1 | 3/2008 | Lee et al. | |
| 2008/0246489 A1 | 10/2008 | Coster et al. | |
| 2008/0264068 A1 | 10/2008 | Nakasuka et al. | |
| 2009/0205963 A1 | 8/2009 | Medoro et al. | |
| 2009/0218223 A1 | 9/2009 | Manaresi et al. | |
| 2010/0035292 A1 | 2/2010 | Levhenko et al. | |
| 2010/0248285 A1 | 9/2010 | Manaresi | |
| 2012/0071335 A1 | 3/2012 | Manaresi et al. | |
| 2012/0091001 A1 | 4/2012 | Manaresi et al. | |
| 2012/0184010 A1 | 7/2012 | Medoro et al. | |
| 2013/0118903 A1 | 5/2013 | Becker et al. | |

FOREIGN PATENT DOCUMENTS

| | | | |
|---|---|---|---|
| JP | 2004000935 A | | 1/2004 |
| JP | 2005501296 A | | 1/2005 |
| JP | 2005507997 A | | 3/2005 |
| JP | 2007017163 | | 1/2007 |
| JP | 2008533487 A | | 8/2008 |
| WO | WO-91/07660 A1 | | 5/1991 |
| WO | WO-91/08284 | | 6/1991 |
| WO | WO-98/04355 | | 2/1998 |
| WO | WO-99/17883 | | 4/1999 |
| WO | WO-00/28313 | | 5/2000 |
| WO | WO-00/47322 A2 | | 8/2000 |
| WO | WO-00/69525 | | 11/2000 |
| WO | WO-00/69565 | | 11/2000 |
| WO | WO-02/12896 | | 2/2002 |
| WO | WO-03/014739 | | 2/2003 |
| WO | WO-03/035895 A2 | | 5/2003 |
| WO | WO-03/045556 | | 6/2003 |
| WO | WO-2004/030820 A2 | | 4/2004 |
| WO | WO-2004/071668 | | 8/2004 |
| WO | WO-2005/060432 | | 7/2005 |
| WO | WO-2005/098395 A1 | | 10/2005 |
| WO | WO-2006/003214 A2 | | 1/2006 |
| WO | WO-2006008602 A2 | | 1/2006 |
| WO | WO-2006/018849 A2 | | 2/2006 |
| WO | WO-2007/010367 | | 1/2007 |
| WO | WO-2007/049103 | | 5/2007 |
| WO | WO-2007/049103 A1 | | 5/2007 |
| WO | WO-2007/110739 | | 10/2007 |
| WO | WO-2007/116312 A2 | | 10/2007 |
| WO | WO-2007049120 A3 | | 10/2007 |
| WO | WO-2007/147018 | | 12/2007 |
| WO | WO-2007/147076 | | 12/2007 |
| WO | WO-2008/112274 A2 | | 9/2008 |
| WO | WO-2009/022222 A3 | | 6/2010 |

OTHER PUBLICATIONS

Fuchs et al., "Electronic sorting and recovery of single live cells from microlitre sized samples," Lab Chip, 6:121-126 (2006).

International Search Report in PCT/IB2008/002873 dated Aug. 3, 2009.

Altomare et al., Levitation and movement of human tumor cells using a printed circuit board device based on software-controlled dielectrophoresis, Biotechnol. Bioeng., 82(4):474-9 (2003).

Berthier et al., NSTI Nanotech 2005, vol. 1 (2005), www.nsti.org.

Cheung et al., Impedance spectroscopy flow cytometry: on-chip label-free cell differentiation, Cytometry Part A, 65A(2):124-32 (2005).

Fiedler et al., Electrocasting formation and structuring of suspended microbodies using A.C. generated field cages, Microsystem Technologies, Berlin, Germany, pp. 1-7 (Dec. 1, 1995).

Final office action, U.S. Appl. No. 12/091,367, mail date Nov. 1, 2011.

Fuhr et al., Positioning and manipulation of cells and microparticles using miniturized electric field traps and travelling waves, Sensors and Materials, 7(2):131-46 (1995).

Gascoyne et al., Dielectrophoresis-based programmable fluidic processors, Lab Chip, 4:299-304 (2004).

Gascoyne et al., Particle separation by dielectrophoresis, Electrophoresis, 23(13): 1973-83 (2002).

Green et al., Ac Electrokinetics: a survey of sub-micrometre particle dynamics, J. Phys. D: Appl. Phys., 33:632-41 (Dec. 10, 1999).

Hughes, Strategies for dielectrophoretic separation in laboratory-on-a-chip systems, Electrophoresis, 23(16): 2569-82 (2002).

International Preliminary Report on Patentability for corresponding International Application No. PCT/EP2005/053235, mailing date Jan. 9, 2007.

International Preliminary Report on Patentability for PCT/IB2006/000636, dated Apr. 29, 2008.

International Preliminary Report on Patentability for PCT/IB2006/001984, dated Dec. 3, 2007.

International Preliminary Report on Patentability for PCT/IB2006/002965, dated Apr. 29, 2008.

International Preliminary Report on Patentability for PCT/IB2007/000751, dated Sep. 30, 2008.

International Preliminary Report on Patentability for PCT/IB2010/000615, dated Sep. 20, 2011.

International Search Report and Written Opinion for corresponding International Application No. PCT/EP2005/053235, mailing date May 2, 2006.

International Search Report and Written Opinion for PCT/IB2006/000636, dated Sep. 8, 2006.

International Search Report and Written Opinion for PCT/IB2006/001984, dated Feb. 27, 2007.

International Search Report and Written Opinion for PCT/IB2006/002965, dated Jun. 15, 2007.

International Search Report and Written Opinion for PCT/IB2007/000751, dated Nov. 16, 2007.

International Search Report and Written Opinion for PCT/IB2010/000615, mailing date Aug. 26, 2010.

Jones, An electromechanical interpretation of electrowetting, J. Micromech. Microeng., 15(6):1184-7 (2005).

Manaresi et al., A CMOS chip for individual cell manipulation and detection, IEEE Journal of Solid-State Circuits, 38 (12):2297-305 (2003).

Medoro et al., A lab-on-a-chip for cell detection and manipulation, IEEE Sensors Journal, 3(3):317-25 (2003).

Medoro et al., A lab-on-a-chip for cell separation based on the moving-cages approach, Proceedings of the 16th Conference on Solid State Transducers, pp. 500-501 (Sep. 15, 2002).

Medoro et al., Dielectrophoretic cage-speed separation of bio-particles, Sensors, Proceedings of the IEEE Vienna, Austria, Oct. 24-27, 2004, pp. 76-79.

Milner et al., Dielectrophoretic classification of bacteria using differential impedance measurements, Electronics Letters, 34(1):66-8 (1998).

Nieuwenhuis et al., Near-field optical sensors for particle shape measurements, Sensors Journal IEEE, 3(5):646-51 (2003).

Nonfinal office action, U.S. Appl. No. 11/724,697, notification date Jun. 7, 2011.

Nonfinal office action, U.S. Appl. No. 11/724,697, notification date Sep. 23, 2010.

Nonfinal office action, U.S. Appl. No. 12/091,367, mail date Mar. 25, 2011.

Nonfinal office action, U.S. Appl. No. 12/294,860, mail date Jan. 27, 2012.

(56) References Cited

OTHER PUBLICATIONS

O'Hara et al., Ratcheting electrophoresis microchip (REM) for programmable transport and separation of macromolecules, Proceedings of the International Mechanical Engineering Congress and Exposition, 3:619-28 (2001).

Office action in corresponding Japanese application No. 2010-531599, dated Oct. 19, 2012.

Office Action, U.S. Appl. No. 11/724,697, notification date Jan. 27, 2012.

Ohta et al., Tech. Dig. of the Solid State Sensor, Actuator and Microsystems, Workshop, pp. 216-219 (2004).

Petersson et al., Carrier medium exchange through ultrasonic particle switching in microfluidic channels, Anal. Chem., 77:1216-21 (2005).

Pethig et al., Enhancing traveling-wave dielectrophoresis with signal superposition, IEEE Eng. Med. Biol. Mag., 22(6):43-50 (2003).

Rousselet et al., Directional motion of brownian particles induced by a periodic asymmetric potential, Nature, 370(6489):446-8 (1994).

Schnelle et al., Three-dimensional electric field traps for manipulation of cells—calculation and experimental verfication, Biochem. Biophys. Acta, 1157(2):127-40 (1993).

Suehiro, The dielectrophoretic movement and positioning of a biological cell using a three-dimensional grid electrode system, J. Phys. D: Appl. Phys., 31:3298-305 (1998).

English translation of Office Action, Japanese patent application No. 2012-167396 (Aug. 2, 2013).

Bonci et al., The miR-15a-miR-16-1 cluster controls prostate cancer by targeting multiple oncogenic activities, Nat. Med., 14:1271-7 (2008).

Final office action, U.S. Appl. No. 11/724,697, mail date Jan. 27, 2012.

International Preliminary Report on Patentability for corresponding International Application No. PCT/IB2009/007316, Jan. 21, 2011.

Klein et al., Comparative genomic hybridization, loss of heterozygosity, and DNA sequence analysis of single cells, Proc. Natl. Acad. Sci. USA, 96(8):4494-9 (1999).

Nagrath et al., Isolation of rare circulating tumour cells in cancer patients by microchip technology, Nature, 450(7173):1235-9 (2007).

Nonfinal office action, U.S. Appl. No. 11/996,068, mail date Jan. 4, 2013.

Nonfinal office action, U.S. Appl. No. 12/091,438, mail date Jul. 25, 2013.

Reichle et al., Combined laser tweezers and dielectric field cage for the analysis of receptor-ligand interactions on single cells, Electrophoresis, 22(2):272-82 (2001).

Romani et al., Capacitive sensor array for localization of bioparticles in CMOS lab-on-a-chip, Proc. Int. Solid State Circuit Conference, 1:224-5 (2004).

Stoecklein et al., Direct genetic analysis of single disseminated cancer cells for prediction of outcome and therapy selection in esophageal cancer, Cancer Cell, 13:441-53 (2008).

Zieglschmid et al., Detection of disseminated tumor cells in peripheral blood, Crit. Rev. Clin. Lab. Sci., 42(2):155-96 (2005).

Examination Report, corresponding European Patent Application No. 08844732.1, dated Apr. 15, 2014.

de Bono et al., Circulating tumor cells predict survival benefit from treatment in metastatic castration-resistant prostate cancer, Clin. Cancer Res., 14(19):6302-9 (2008).

\* cited by examiner

METHOD AND APPARATUS FOR THE IDENTIFICATION AND HANDLING OF PARTICLES

CROSS REFRENCE TO RELATED APPLICATIONS

This is the U.S. national phase of International Application No. PCT/IB2008/002873, filed Oct. 28, 2008, which claims the benefit of Italian patent Application No. TO2007A 000771, filed Oct. 29, 2007.

FIELD OF APPLICATION

The present invention concerns miniaturised methods and devices for the handling of cells. In particular, the invention relates to methods and devices for optimised selection and isolation, within a more or less numerous population, of elements of interest and/or utility for a series of subsequent operations.

The invention is applied mainly in the implementation of biological protocols on samples of cells in a reduced volume of a suspension medium, which require accurate control of individual cells or particles in order to perform handling of said cells or particles.

STATE OF THE ART

Numerous experimental protocols exist which require accurate and careful selection of particles having specific characteristics within a population constituting the sample. The possibility of identifying, on the basis of the values taken on by at least one parameter of interest, the particles of the population that meet certain criteria and which are therefore suitable for successfully undergoing the subsequent phases of the experimental protocol is crucial, not only in speeding up and therefore, generally, reducing the costs of the experimental campaign, but also and above all when the cells of interest are rare within the population.

Diagnostic experimental protocols, among others, are known based on the handling of cells (or, more generally, particles) the concentration of which, within the sample, is particularly low and in which, therefore, the cells of interest have to be identified and isolated on the basis of their distinctive characteristics with an extremely high sensitivity, in order not to run the risk of losing cells/particles of interest.

For example, EP0500727 (Bianchi) describes an experimental protocol for the prenatal diagnosis of chromosome abnormalities based on obtaining, from a sample of peripheral maternal blood, a population enriched in nucleated fetal cells (erythroblasts) which then undergo a series of genetic type diagnostic procedures (for example FISH, QF-PCR, etc.).

WO2006018849 [MonaLiza Medical] describes the possibility of performing analogous genetic type diagnostic procedures on fetal trophoblasts obtained by means of appropriate enrichment of a maternal transcervical sample (TCC).

In both cases, according to the known experimental protocol, it is necessary to identify which cells are nucleated in order to be able to subsequently proceed with analysis of the chromosomal heritage. Furthermore, it is essential to discriminate between fetal cells and maternal cells, in order to avoid false positives/negatives. It may also be necessary to perform further controls, aimed at excluding the possibility of false positives.

In general, therefore, for one or more characteristic parameters of the cells/particles of interest detectable by means of one or more corresponding sensors, a threshold value is established on the basis of which the selection is made.

For example US20060139638 discloses a method for identifying and selecting by dielectrophoresis live cells of interest within a cell population also comprising dead cells or cell clusters. The selection is made following processing of the luminosity distribution within a cell which allows some characteristic parameters of the cell to be obtained, for example the dimension. Only the cells that have a dimension below a certain value are selected as they are considered to be of interest. In this way, however, since the value of the dimension parameter is established before examination of the particles of interest, often only a very small fraction of the cells/particles of the population is actually isolated. It is even possible for none of the cells of interest to be selected for the subsequent phases of the protocol (no call). However, this does not always imply that none of the cells of the population are actually usable. Given the significant variability of the distribution of the characteristics of interest in the cellular population from one subject to another, from one sampling to another, or even more simply due to possible alterations in the experimental and instrumental conditions, the pre-established threshold value may be so high that the selection procedure leads to the isolation of too few useful cells to successfully complete the subsequent analyses. On the other hand, if the threshold value is too low or if, for example, the distribution of the values of the parameter of interest within the cellular population is multimodal, the selection procedure may not be accurate enough (i.e. non-useful cells are also selected), or it may privilege a portion of the sample that is not representative of the entire cellular population.

FIG. 11 shows the selection of particles determined within a population of particles as in the known art, i.e. using a threshold value determined a priori, i.e. before examination of the entire sample.

If the pre-set threshold value is too low as in FIG. 11 (A), non-useful cells are also selected, i.e. the selected particles are contaminated. On the other hand, if the pre-established threshold value is high as shown in FIG. 11 (B), the selection procedure leads to the isolation of a reduced number of useful cells.

Consequently, the tests frequently have to be repeated, new samples have to be taken or, more simply, part of a useful sample is wasted, with consequent loss of information.

In some cases an a priori assessment of the properties of the sample is performed, examining a portion of it. On the basis of the information collected in this phase, threshold values are established for the parameters of interest and, subsequently, the actual selection is performed on what is left of the sample. This method is disadvantageous, firstly because it involves sacrificing a part of the sample for the preliminary assessment and secondly because the pre-established threshold values can no longer be adapted if the portion of sample examined a priori turns out to be not representative of the characteristics of the entire sample.

As known, various techniques for handling of particles inside microfluidic devices also exist.

One method uses dielectrophoresis potential cages while other methods involve the use of laser microdissection or optical tweezers.

The drawback of handling by laser microdissection is that parts of interest (single cells or clusters, etc.) are handled by dissecting the sample together with the support to which it adheres. Furthermore, the laser microdissection phase cannot be applied to cells or particles immersed in a fluid.

Another known method is to place bodies inside fluids and handle them by optical means. With laser-tweezers it is possible to maintain particles in solution with great accuracy and move them in a predetermined manner.

This type of handling has drawbacks, however, because the particle inside the laser beam which traps it is subject to thermal collisions and therefore its position can be accidentally modified at random. Furthermore, only one particle at a time can be moved and the position of each particle of a population cannot be controlled.

DISCLOSURE OF INVENTION

The aim of the present invention is therefore to provide a method and a device for the identification and handling (with consequent selection and/or isolation) of rare particles within a population of interest, overcoming the drawbacks previously described.

In particular, one object of the invention is to provide a method for identifying and selecting rare particles rapidly and with high sensitivity, therefore limiting analysis costs and times and avoiding wastage of useful sample or loss of information.

According to one aspect of the present invention, a method is provided as claimed in claim 1.

According to a further aspect of the present invention, an apparatus is provided as claimed in claim 15.

BRIEF DESCRIPTION OF THE DRAWINGS

Further advantages and characteristics of the present invention will become evident from the following description of a preferred embodiment, provided purely by way of non-limiting example and with reference to the figures of the accompanying drawings, in which.

BEST MODE FOR CARRYING OUT THE INVENTION

Figure 1:
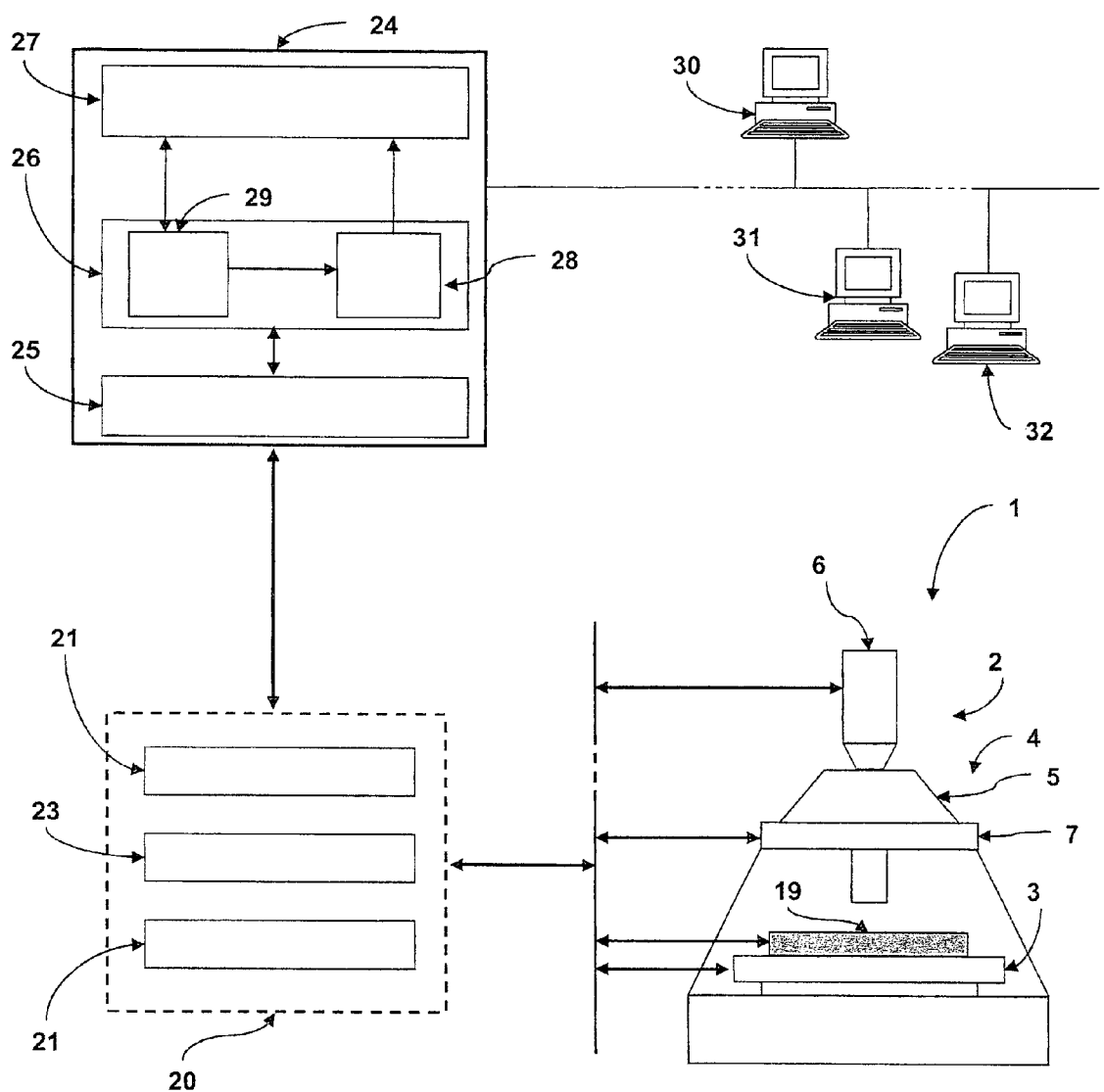
FIG. 1 is a schematic representation of a system which provides the method for optimised selection of particles according to the invention.

The system 1 for optimised particle selection illustrated in FIG. 1 is based on the use of commercial technology and comprises an upright epifluorescence microscope (Olympus) 2 comprising a frame (not illustrated) which supports a motorised horizontal surface 3 (or also stage) and an optical system 4 positioned above the horizontal surface 3.

The horizontal surface 3 is equipped with nano-stepper motors with extreme positioning accuracy (~±3 mm) on the X-Y plane and is sustained by a support (not illustrated), equipped with nano-stepper motors with extreme positioning accuracy (~±0.01 mm), mounted in a sliding manner on a vertical slide connected to the microscope frame to permit exact definition of the focus on the Z axis.

The optical system 4 comprises an illuminator (not illustrated), a set of fluorescence filters (not illustrated) and a movable optical unit 5 which comprises a CCD Camera (Orca ER Hamamatsu) 6 with 1600×1200 mega-pixel resolution and a revolver turret 7, equipped with several lenses with different magnifying powers, which can rotate to position the chosen lens above the motorised surface 3.

The illuminator and the filter system defining the epifluorescence system comprise a broad spectrum white light source, a first filter block (FITC block) with an excitation filter 460-495 nm (blue), emission filter 515-550 nm (green) and dichroic mirror at 505 nm, and a second filter block for bright-field illumination and are fixed to the frame of the microscope 2.

Figure 9:
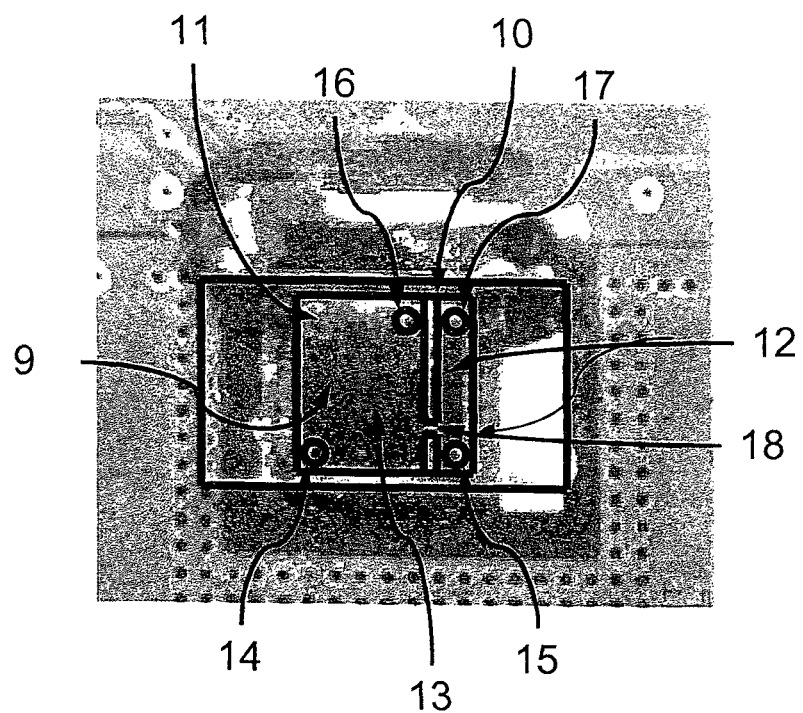
FIG. 9 is an image which shows a hybrid device or silicon/plastic chip for the handling of particles according to the method of the invention.

FIG. 9 illustrates a silicon/plastic hybrid microfluidic device 8 (or also chip) for the handling of particles in suspension in a liquid as described in Lab Chip 2006, 6, 121-126. The chip 8 comprises a particle handling chamber 9 with dimensions 16 mm×16 mm and defined by a base wall, an upper wall, substantially parallel to the base wall, and a spacer element which is positioned between the base and upper walls to maintain the base and upper walls at a certain distance equivalent to its height. The handling chamber has an internal chamber which is delimited at the top and bottom by the upper wall 13 and the base wall respectively, and laterally by the spacer element. The internal chamber has a substantially parallelepiped shape with square base and comprises a separation wall 10 arranged parallel to a lateral wall of the internal chamber which defines two chambers 11,12 with substantially parallelepiped shape and rectangular base limited laterally by the separation wall 10, the first of which 11 constitutes a sample loading chamber (approximately 2.9 µl) and the second 12 a sample recovery chamber (approximately 0.6

μl). The separation wall 10 has an interruption 18 with width of 300 μm in the vicinity of a lateral wall of the internal chamber which constitutes the communication channel 18 between the sample loading chamber 11 and the sample recovery chamber 12.

The upper wall 13 of the handling chamber, with substantially parallelepiped shape and square base, is transparent, made of polycarbonate and has four apertures 14,15,16,17, two of which 14,15 are positioned in the loading chamber and two 16,17 in the recovery chamber, which are suitable for connecting the internal chamber with the outside.

The base wall of the internal chamber is provided with an array or grid of dielectrophoresis electrodes which constitute the surface of the chip 8, each of which can be individually controlled to create dielectrophoresis cages able to handle individual particles inside the grid. According to one aspect of the method according to the invention, the particles are handled after each of them have been captured in a specific site of a plurality of sites made available by activation of the electrodes constituting the surface of the chip 8. Analogously to the physical structure of the chip 8, the sites in which the particles are captured are also arranged inside the handling device according to an array.

It should be noted that the chip 8 is provided with two different and distinct chambers (11,12), hydraulically connected and delimited on at least one face of the base wall of the chip. Alternatively it is possible to provide separate chips, hydraulically connected to each other.

The chip 8 furthermore comprises a printed circuit to which the handling chamber is glued, in which the electronic circuits for separately controlling the individual electrodes of the array and a set of contacts heading the electronic circuits are defined.

The chip 8 constitutes a microfluidic device for the handling of particles, or preferably cells, which can advantageously be used as a disposable device.

In use, when one of the apertures 14 (16) of the loading chamber 11 is used by an operator to deposit a sample (in a substantially liquid phase) in the internal chamber, the other aperture 16 (14) of the loading chamber 11 acts as a vent. In view of the reduced dimension of the communication channel between the loading chamber 11 and the recovery chamber 12, an air/water meniscus forms in the channel which prevents the sample from penetrating the recovery channel. Subsequently the recovery chamber 12 is filled with a buffer solution which prevents the particles present in the sample solution from penetrating the recovery chamber 12.

Once the sample has been deposited in the chip 8, the device is placed on the motorised surface 3 and positioned by means of screws (not illustrated) in a suitable housing 19 obtained in the motorised surface.

Said housing 19 comprises the connectors (not illustrated) to which the control system of the dielectrophoresis electrodes is connected; during use the coupling between the contacts of the handling chip 8 and the connectors present in the horizontal motorised surface 3 permits the control of each dielectrophoresis electrode.

In order to recover the cells of interest present in the sample solution, a path P is defined in the base wall of the internal chamber of the chip 8, consisting of a set of dielectrophoresis electrodes. Said path defines an outlet which extends through the communication channel 18 to transport cells of interest from an initial point P1 of the loading chamber 11 to a final point P2 of the recovery chamber 12. By activating in succession the dielectrophoresis electrodes present in the path P in the direction of the recovery chamber 12, the cells of interest are moved from the sample solution to the buffer solution, in which they are immersed and then recovered.

As illustrated in FIG. 1, the system 1 for optimised particle selection furthermore comprises an external control unit 20 connected to the microscope 2 by means of electric cables (not illustrated), which is housed in one or more external units (not illustrated), some of which can also be mechanically supported by the frame of the microscope 2. In particular, the control unit 20 comprises a first control device 21 for management of the motorised stage 3, a second device 22 for management of the optical unit and acquisition of the images from the camera and a third device 23 for management of the control signals of the dielectrophoresis electrodes.

It should be noted that the external control unit 20 can comprise an industrial computer of known type connected by means of an Ethernet network (preferably operating according to the TCP/IP protocol) to the external units or alternatively can comprise one or more external units provided by means of dedicated electronics, connected to one another by Ethernet network (preferably operating according to the TCP/IP protocol).

Furthermore, the system 1 for optimised particle selection comprises one or more user interface devices 24 (of which only one is shown in the figure) also called "HMI" (Human Machine Interface) devices. Each HMI device 24 comprises a computer of known type provided with a screen (not illustrated in FIG. 1) for display of the data and a keying-in device (not illustrated in FIG. 1), which is normally defined by a keyboard and/or a pointing device and can also be integrated in the screen by means of the touch-screen function. Each HMI device 24 allows an operator to interact with the control unit 20 of the microscope 2 allowing said operator, for example, to send configuration information relative to the camera 6, select and subsequently position the chosen filters or lenses of the revolver 7 or move the motorised stage 3 to a given position so as to display the cells present in a certain position on the surface of the handling chip 8 following the loading of a sample.

Further computers 30, 31, 32, which can be arranged in local or remote configuration, can be connected to the HMI device 24 via an Ethernet network (preferably operating according to the TCP/IP protocol). For example a computer 30 is an industrial or office computer, located in a laboratory or in any case in a space reserved for laboratory analyses, a computer 31 is an office computer and is located in the same building as the laboratory, a computer 32 is an office computer and is located at a considerable distance from the laboratory. The computers 30 and 31 are connected to the HMI device 24 solely via an Ethernet/Intranet type network, while the computers 32 are connected to the HMI device 24 via the Internet. It should be noted that the computers located at a considerable distance from the laboratory are able to display the same data as the computer located in the laboratory.

The HMI device 24 comprises a first communication device 25 which dialogues (i.e. exchanges data in a bidirectional manner) with the control unit of the system for optimised particle selection, a storage device 26 which also implements a database (for example SQL, SQL Light etc.), and a second communication device 27 which dialogues (i.e. exchanges data in a bidirectional manner) with the user. The first communication device 25 provides the access protocol to the data of the control unit and implements the control commands of each different peripheral device present, for example motorised stage 3, movable optical unit 5, camera 6.

The second communication device 27 provides the real graphic user interface.

The two communication devices dialogue mainly with each other only indirectly, i.e. they dialogue with each other via the storage device 26; in other words, barring specific commands with which the user controls specific devices, the first communication device 25 reads/writes data in the storage device 26 and at the same time the second communication device reads/writes data in the storage device 26 in an essentially random manner (i.e. when the operator decides to use the user interface).

The first communication device 25, the second communication device 27 and the storage device 26 are usually provided by respective programs (software) which constitute as a whole a particle handling program (software). In particular, the program (software) which provides the second communication device 27 constitutes the graphic user interface and provides image processing means via which the parameters p1 . . . pn characteristic of each particle are extracted. Analogously, the program (software) which provides the second communication device 27 provides more generically means for processing of at least one function of the parameters detected. Furthermore, the same program (software) that provides the second device 27 constitutes means for selection of particles, and means for establishing a selection criterion to be used as a reference parameter for making said selection.

Said programs are usually resident in the computer forming part of the HMI device 24 but alternatively can be resident in other computers positioned locally or remotely and exchange data via the Intranet and/or Internet networks.

In use, the entire surface of the chip is scanned and a number of images are acquired and stored in an area 28 of the storage device (15 partially, superimposed images for each line totalling 20 lines) permitting accurate assessment of the chip content with an appropriate degree of definition. The images stored are processed by means of graphic editing which allows identification of the cells present and, for each cell identified, storage of the characteristic data of each cell, i.e. the parameters p1 . . . pn, in the storage device in an area 29 implementing a database SQL.

It should be noted that alternatively or parallel to scanning of the entire surface of the chip by means of an external sensor such as the camera, it is possible to use sensors (not illustrated) inside the chip to detect the characteristic data of each cell. As described in WO2007/049103, the content of which is understood to be incorporated here for the parts necessary for simple reference, it is possible for example for the surface of the chip 8 to comprise both dielectrophoresis electrodes and optical (or impedenziometric) sensors able to detect the parameters p1 . . . pn characteristic of each cell.

It should furthermore be noted that the handling of each cell can be successfully performed by means of handling techniques alternative to dielectrophoresis (for example optophoresis trapping, electrowetting on dielectric—EWOD), on condition that the cells are handled in microfluidic devices, each one having been captured in a generic site of a plurality of sites that can be individually controlled.

Figure 2:
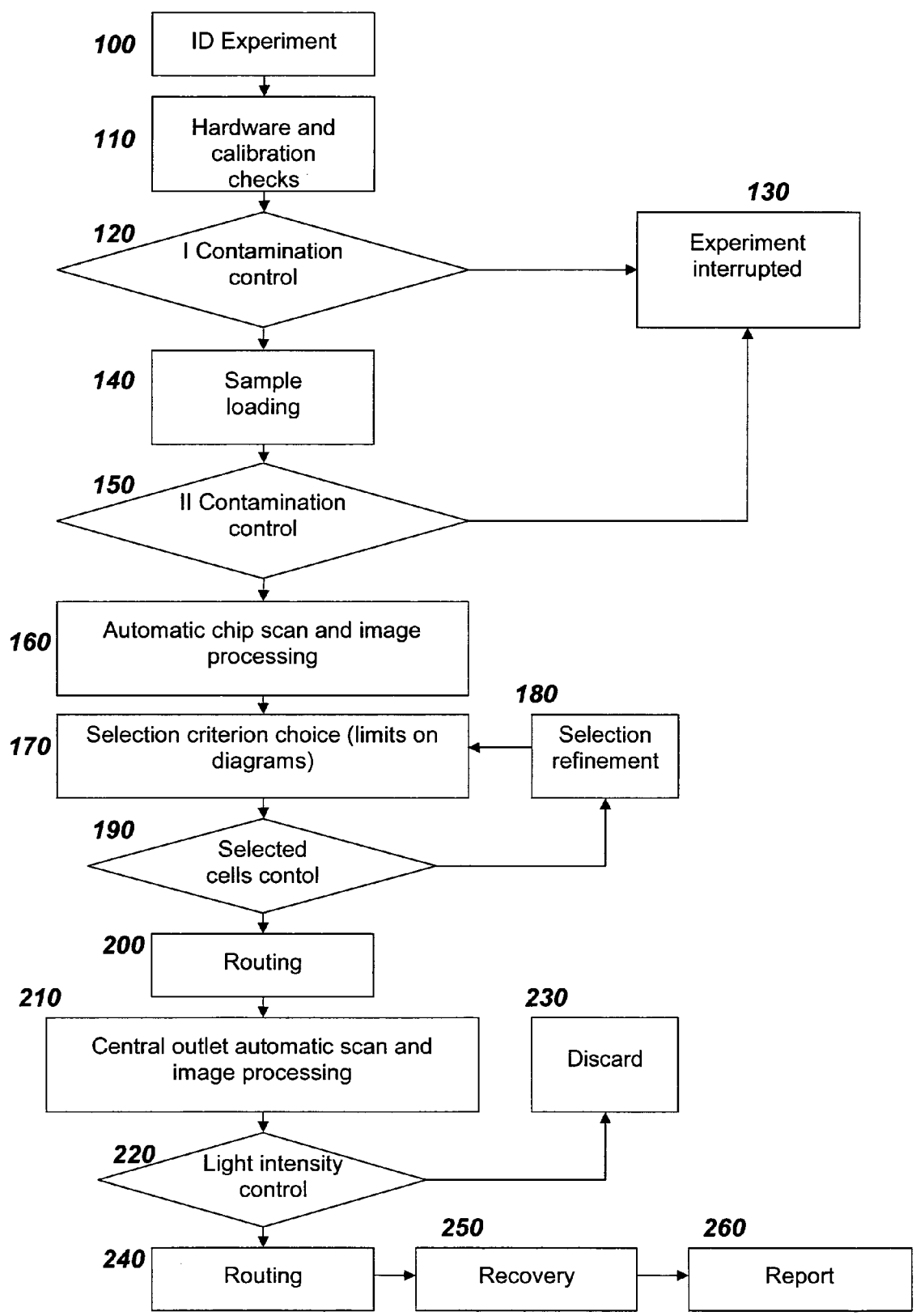
FIG. 2 is a flow chart of the phases of the method of the invention.

By way of non-limiting example, a preferential embodiment of the method according to the present invention will now be described, following the flow chart shown in FIG. 2.

To start (block 100), the experiment to be carried out is identified by collecting information concerning the operator and the sample to be analysed. The system then performs in automatic mode (block 110) a series of operations to verify correct connection and/or configuration and/or calibration of the control unit 20 in relation to the devices constituting the microscope 2, thus guaranteeing correct operation during the experiment. A preliminary check is generally scheduled (block 120) in order to ensure that no contaminants are present on the surface of the chip 8, and more particularly along the path P of the outlet. If this check identifies the presence of contaminants, the experiment is interrupted (block 130) whereas if the result is negative, the sample is deposited (block 140). Verification of the absence of contaminants is repeated at this point (block 150) to exclude the possibility of introduction of other undesired substances onto the surface of the chip together with the sample to be analysed. In the case of contamination, the operator can obviously recover the sample previously deposited so that it can be re-used in another experiment.

Having completed this check, the actual analysis phase can be initiated. The entire surface of the chip is scanned (block 160) in automatic mode and by means of an appropriate graphic editing process, a set of characteristic data of each particle, i.e. the parameters p1 . . . pn, are identified and stored in the database (or also storage means).

Having acquired the images of the entire surface of the chip and stored the characteristic parameters of each particle, the operator can establish a criterion for selection of the particles of interest after acquiring information on the entire sample (block 170) (the selection criterion can for example be the choice of particles with a certain morphology, the choice of the brightest particles or the choice of rare particles with certain characteristics). In particular, the selection criterion is established on the basis of the result of processing of the data acquired for each particle.

Figure 3:
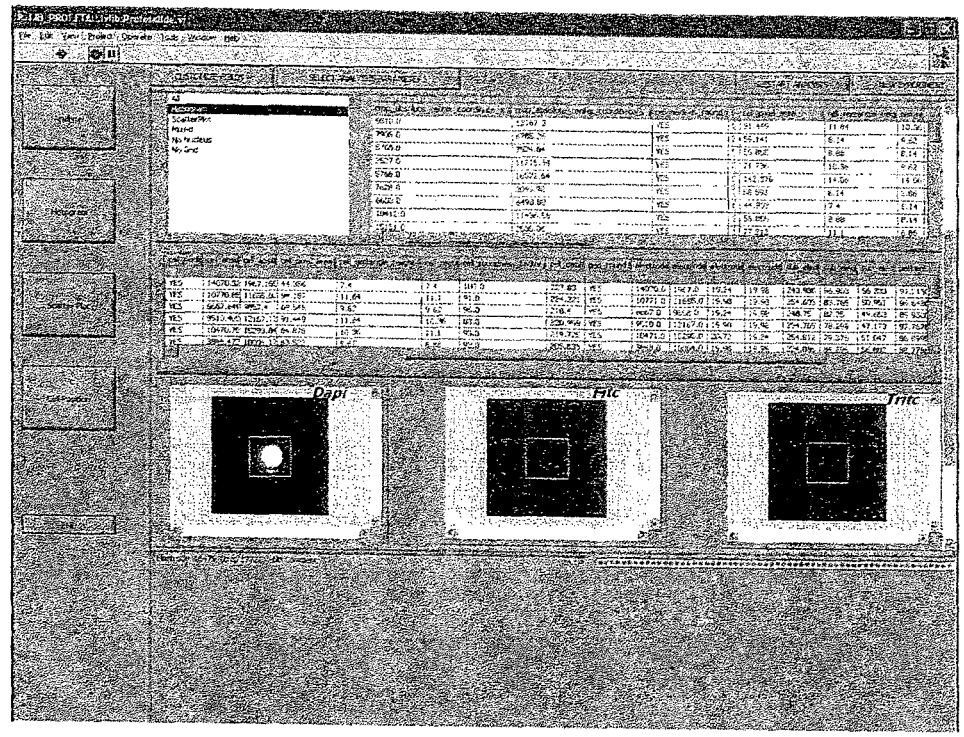
FIG. 3 is a reproduction of a screenshot of the interface of a program for implementation of the optimised particle selection method according to the invention, containing a list of particles observed and selected; for each of these, respective measured values of a plurality of experimental parameters and the images acquired by scanning the sample in one or more light channels at different wavelengths are shown.
Figure 4:
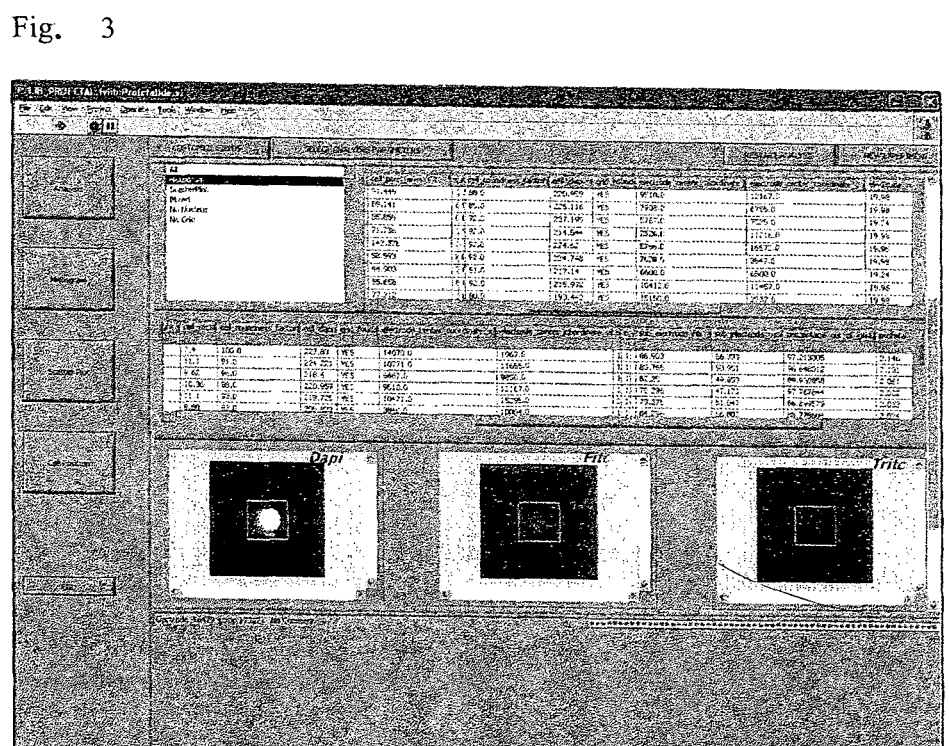
FIG. 4 is a further reproduction of the screenshot of the program of FIG. 3 showing, for each of the particles observed in the list, respective measured values of a further plurality of experimental parameters and the relative images acquired by scanning the sample.

At a practical level, the graphic interface shows the operator a screenshot (FIGS. 3 and 4) containing the list of the particles, cells in this specific case, observed by optical scanning of the entire sample. For each of them, the values of a multiplicity of experimental parameters measured during the scanning can be shown, such as optical parameters (transparency, opacity, uniformity of luminous intensity), morphological parameters (area factor or also indirect measurement of the beam in pixels, form factor, roundness or sphericity factor etc. . . . ), correct positioning inside a cell (site) of the grid of the chip 8, luminosity measured in light channels corresponding to different wavelengths etc. Generally speaking, the parameters measured for the particles can also refer to the bio-electrical and/or bio-chemical properties (for example it is possible to establish whether a cell is alive or dead by studying over time the decay in the fluorescence of cells marked with calceine or, by analysing images taken at a certain time interval, measure the absorption of a dye etc.), or mechanical properties (for example the elasticity of a particle can be determined by subjecting it to a dielectrophoresis impulse able to deform it; by observing the time necessary for the particle to return to its original form, a factor of elasticity of the particle can be deduced), or dielectric properties (if the particle observed locates in a cell of the grid of the chip 8, then we are dealing with particles that can be manipulated by means of NDEP, whereas if the particle locates between adjacent cells of the grid of the chip 8, then we are dealing with particles that can be manipulated by means of PDEP), or—in the case of cells—the expression of surface or intra-cytoplasmatic antigens, or an appropriate combination of them. The data are acquired via the use of a plurality of sensors, which can be internal or external to the hybrid device 8.

For said purpose, the method according to the invention can also comprise a phase of marking the particles (or cells, in this case) in suspension with at least one marker which can be detected by means of one of said sensors inside and/or outside the chip. For each of the cells, the coordinates which define their arrangement with respect to the surface of the chip 8 are furthermore stored and shown.

Via a further screenshot (FIG. 5) the operator is shown diagrams illustrating the distribution, with respect to the cell population, of the value of the experimental parameters p1, p2, ... pn measured during the scanning and stored, and/or the value of one or more functions of at least one of said parameters appropriately processed by the system. By appropriately defining a selection criterion, the operator can use the interface to select a subset of particles of the population in question: by modifying the position of the cursors 34 in the histograms of FIG. 5, the operator can set threshold values below and/or above the parameters measured and/or below and/or above respective functions of the same.

Said lower or upper threshold values and/or said intervals of interest (for example corresponding to a portion of interest of the function of the parameters $p_i$ processed and associated with the selection criterion, or to a portion of the distribution of the value of said function within the population of particles, and therefore between a lower threshold value and an upper threshold value) constitute a "threshold criterion" with which the value of the function of the parameters $p_i$ is compared in order to perform selection of the particles of interest.

Said threshold values can be chosen by the operator after assessing the properties of the cell sample as a whole, in particular on the basis of the value processed by the system of the functions of the parameters stored, or a procedure can be automatically implemented that identifies the particles responding to a certain selection criterion, which can vary from experiment to experiment, on the basis of the data collected for the entire population tested.

It should be furthermore noted that, in the latter case, the operator can choose whether to implement the automatic selection procedure for the final selection or alternatively control the automatic selection proposal, refining it via manual checking of the results.

It is important to underline that threshold values of the quantities of interest in the experiment are not established a priori; on the basis of the information relative to the entire sample obtained by means of the scanning, the selection criterion and consequently the relative threshold values are chosen in an adaptive manner, in order to identify and handle the cells that meet given requirements.

Therefore, according to the method of the invention, it is possible to select the cells having the best characteristics overall for the subsequent use envisaged, i.e. those for which the value of an appropriate merit function defined on a time by time basis is optimised.

In this way the user interface 27 constitutes means for selection of particles and, furthermore, means for establishing a threshold criterion to be used as a reference parameter for the selection.

According to the subsequent destination of the cells—for example use in further experiments—the selection criterion can be modulated so as to obtain a sufficient number of cells that meet given requirements making them suitable for the following experimental step.

Figure 5:
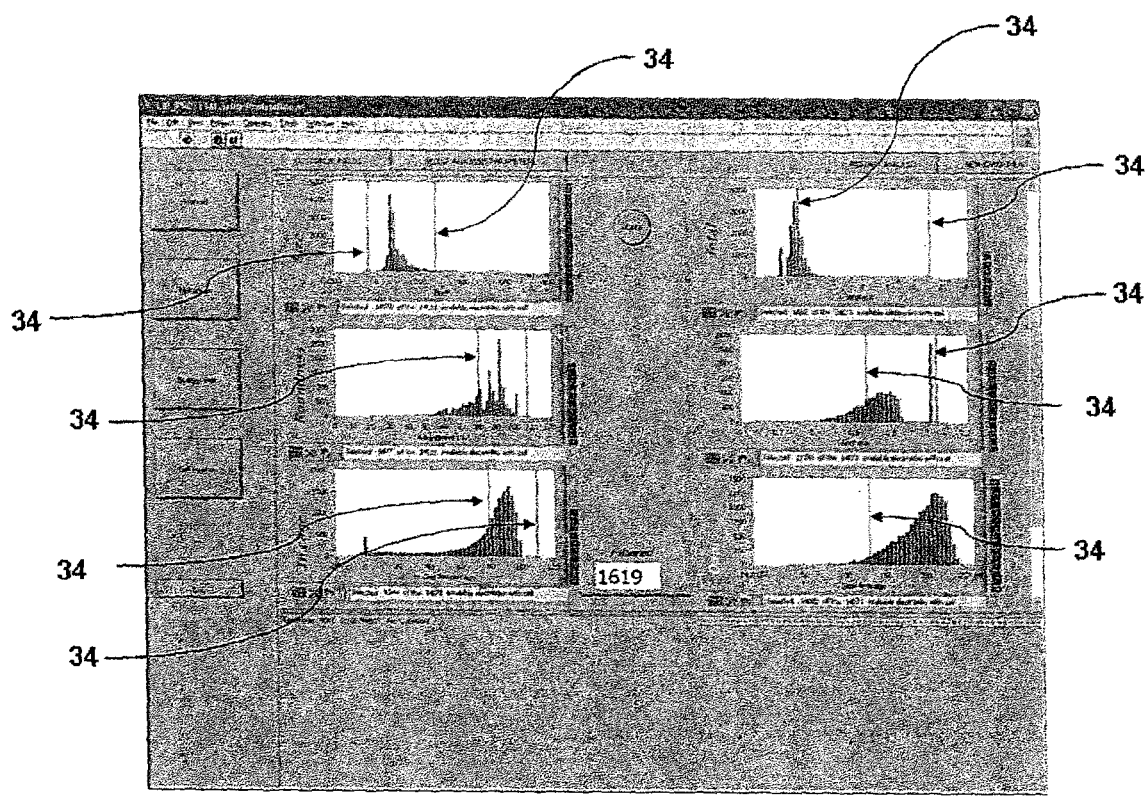
FIG. 5 is a reproduction of a further screenshot of the interface of a program for implementation of the optimised particle selection method according to the invention, showing for a selectable observed particle a multiplicity of histograms representative of the trend of one or more experimental parameters measured for the particle.

Defining the thresholds of interest via the interface of FIG. 5 (block 170), the operator simultaneously performs a selection within the population of particles, identifying those for which the values of the parameters p1, p2, ..., pn have been measured and for which the values of the functions falling within the intervals of interest defined by the thresholds graphically set with the cursors 34 have been calculated.

The operator is assisted if necessary in positioning the cursors 34 in the histograms of FIG. 5: on request, the interface shows a further screenshot (not illustrated) for each histogram bar with the images of the particles associated with that bar.

By way of non-limiting example, FIG. 5 shows, in a first column, histograms relative to the distribution, in the population tested, of morphological characteristics of the particles such as dimension, roundness factor and correctness of positioning in one of the cells of the device used for the handling. In a second column on the right of the previous one, are histograms showing the trend of complex functions based on a suitable combination and/or processing of different parameters measured which can be used as indexes of non directly measurable properties. As a combination example, the results relating to measurements of luminosity performed at different wavelengths can be combined, each corresponding to a specific marker associated with the presence/absence of a certain characteristic (for example of the cellular nucleus, of a specific antigen, of spontaneous fluorescence of the particle, etc.). As a processing example, the results relative to luminosity measurements can be processed to take into account and if necessary compensate for different illumination by the illuminator in different areas of the chip 8.

After performing the selection within the particle population by means of the interface of FIG. 5, the user can subsequently refine the selection already made (block 180—Selection Refinement). For the particles that meet the threshold criteria established via the screenshots of FIG. 5 (block 190), the user can check the particles selected since, via the screenshots of FIGS. 3 and 4, he can view, for each particle, both its characteristic parameters and the images acquired during scanning of the sample. These images, displayed in one or more light channels at different wavelengths (by way of non-limiting example in FIGS. 3 and 4 the images of cells in the DAPI, FITC and TRITC channels are shown), allow the operator to decide whether to definitively select or not a particle initially pre-selected and therefore the screenshots of FIGS. 3 and 4 constitute control means for refining the selection already made. In fact, although the particle has been initially pre-selected, it may be an impurity and therefore not useful for the purposes of the subsequent experimental protocols.

The graphic user interface 27 also offers the operator a further means of control for refining the selection already made, consisting in the possibility of viewing each particle selected through the microscope eyepieces. By activating a control button (not illustrated), the particle selected is automatically positioned right below the microscope lens and this allows the operator to view the particle via the eyepieces.

It should be noted that the particle selected is automatically positioned below the microscope lens since, when the control button is activated, the graphic user interface 27 communicates to the control unit 20 the coordinates of the particle of interest inside the grid of the chip 8 and the control unit 20 accurately moves the stage stored on the plane X-Y in order to align the particle (position inside the grid of the chip 8) with the microscope lens. If necessary, the control unit 20 automatically moves the motorised stage along the Z axis to focus the selected particle.

At the end of said further control phase, the operator can decide whether the particle is of interest or if it should be considered an impurity.

In this way the graphic user interface 27 constitutes means for selection of particles and, furthermore, control means for refining selection of the particles of interest. If the sensor is external to the microfluidic device and consists of a camera or even if the sensor is internal to the microfluidic device and consists of an optical sensor, the control means comprise means for displaying the images of each particle.

Figure 6:
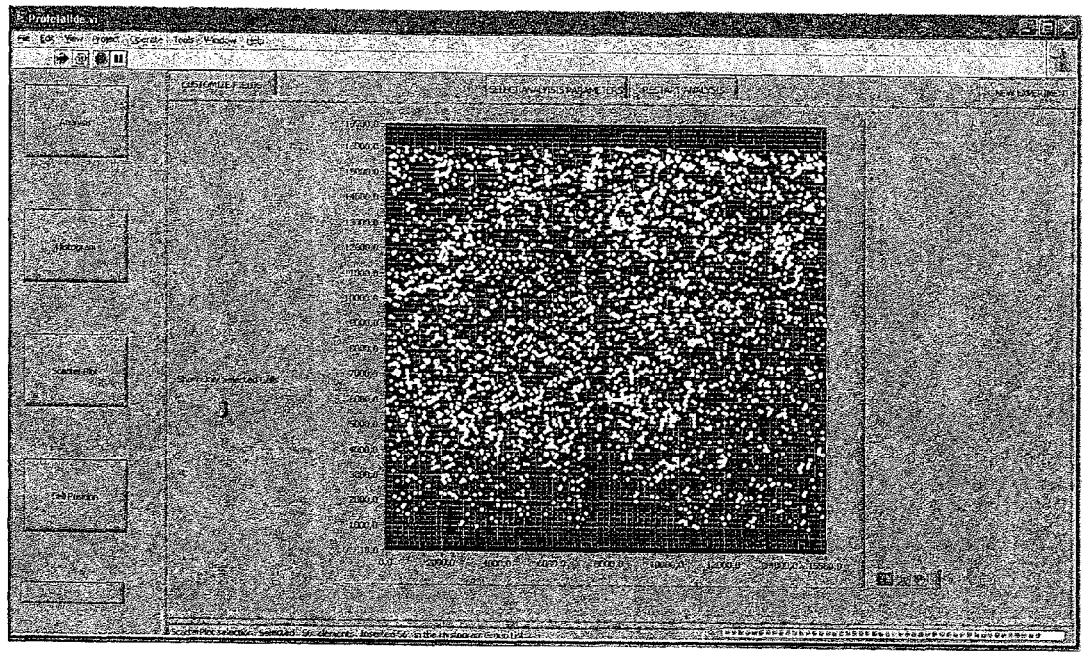
FIG. 6 is a reproduction of a further screenshot of the interface of a program for implementation of the optimised particle selection method according to the invention, showing simultaneously all the particles observed so as to reproduce their actual arrangement in the sample scanned.
Figure 7:
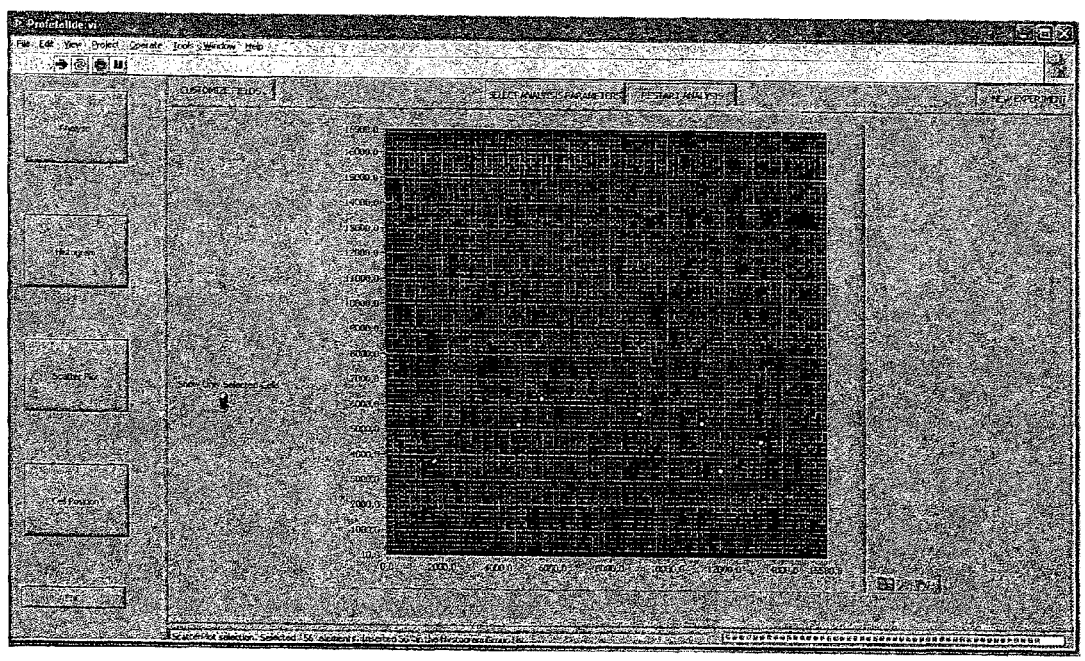
FIG. 7 is a reproduction of a further screenshot of the interface of a program for implementation of the optimised particle selection method according to the invention, showing only the particles selected according to the method so as to reproduce their actual arrangement within the sample scanned.

The interface offers the operator further possibilities: it is possible to observe the arrangement on the surface of the chip of all the particles of the sample (FIG. 6) or only the particles actually selected (FIG. 7), establishing the threshold values in an adaptive manner as described above. It should be noted that the coordinates of the particles shown in the screenshot of the interface of FIG. 6 correspond to those of the sample in the chip 8, and therefore have a distribution that reflects the relative physical structure. In particular, it is possible to identify in the lower part of the screenshot of FIG. 6 a horizontal band in which no particles are present, which corresponds to the recovery chamber 12 for the selected particles. Analogously, no particles appear in the upper portion because that portion of the loading chamber 11 is used to house any discarded particles.

Figure 8:
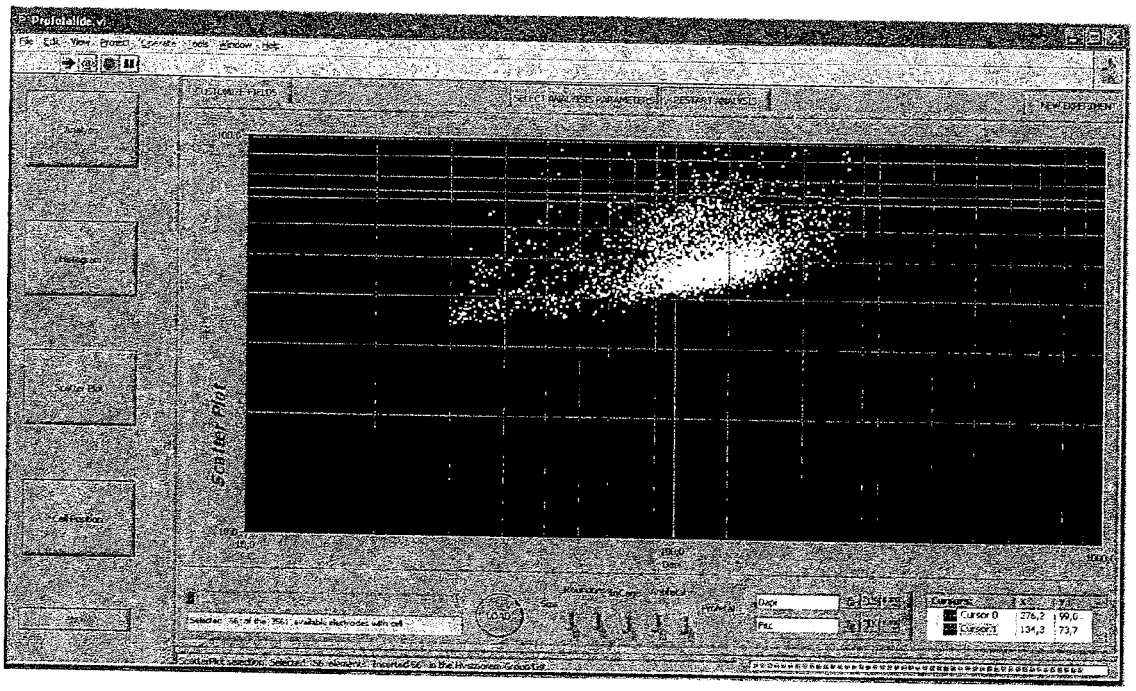
FIG. 8 is a reproduction of a further screenshot of the interface of a program for implementation of the optimised particle selection method according to the invention, in which the values relating to two experimental parameters measured for the population of particles are shown in a dispersion diagram.

FIG. 8 shows a further screenshot of the interface in which the operator can view, in the form of a dispersion diagram, the distribution of two parameters or functions of interest in the particle population. By way of non-limiting example, FIG. 8 shows the luminosity values measured at two different wavelengths, each corresponding to a specific marker. Via the use of appropriate commands, the operator can view in an analogous dispersion diagram the values relative to other parameters and/or functions. Also via this form of display, the operator can set threshold values so as to define an appropriate selection criterion and simultaneously select the particles that respond to said requirements, as discussed previously with reference to representation by means of histograms.

Having the completed this phase, having defined a selection criterion and having substantially performed an initial selection of the particles that meet said criterion, the next step in the procedure (block 190) involves control (if necessary even one by one) of the particles selected in the previous step, refining said selection if necessary.

The operator can then confirm the selection of the particles made in the previous phase having analysed overall the entire population contained by the chip, verifying the correctness of his choice since he can analyse the specific characteristics of each individual cell in detail. The possibilities offered by the interface include that of ordering the particles according to the value of any one of the fields available, for example according to the increasing light intensity in the DAPI field in the case of cells, if the intention is to select the "best" cells for a series of subsequent experiments, or if the user wishes to select cells with light intensity values similar to one another in a specific channel.

If the user is not satisfied with the choice already made, he can return (block 180) to the preceding phase so as to further refine the selection, if necessary varying the selection criterion previously established. If on the other hand the result of the selection is quantitatively and qualitatively satisfactory, the next step in the method is to proceed with a first transfer or routing phase (block 200), i.e. automated handling of the particles with the aim of transferring the particles selected from the position originally occupied on the surface of the chip to a position, also stored by the system, in the outlet for conveying the particles towards the recovery chamber 12. This constitutes the first part of the journey of the selected particles towards the recovery chamber. According to the specific geometry of the handling device used each time, one single central outlet can be provided, or the device can comprise several outlets in parallel in order to accelerate and facilitate the routing operation. Said operation separates the particles of interest previously selected, handling only these particles within the sample.

At this point, the method schedules a further control step (block 220) on the outlet obtained by performing a new scan (block 210) to acquire the images of the outlet and the particles contained in it. On the basis of the information obtained from these images, the user will decide, from among all the particles selected in the first transfer phase, which particles/cells to discard and which to extract from the chip and convey to the recovery chamber 12.

Said further control phase is performed by comparing for each particle the photograph of the particle in its original position and in its position in the outlet in order to ensure that the first transfer phase has actually handled the selected particle, which may not arrive correctly at its destination in the outlet.

Figure 10:
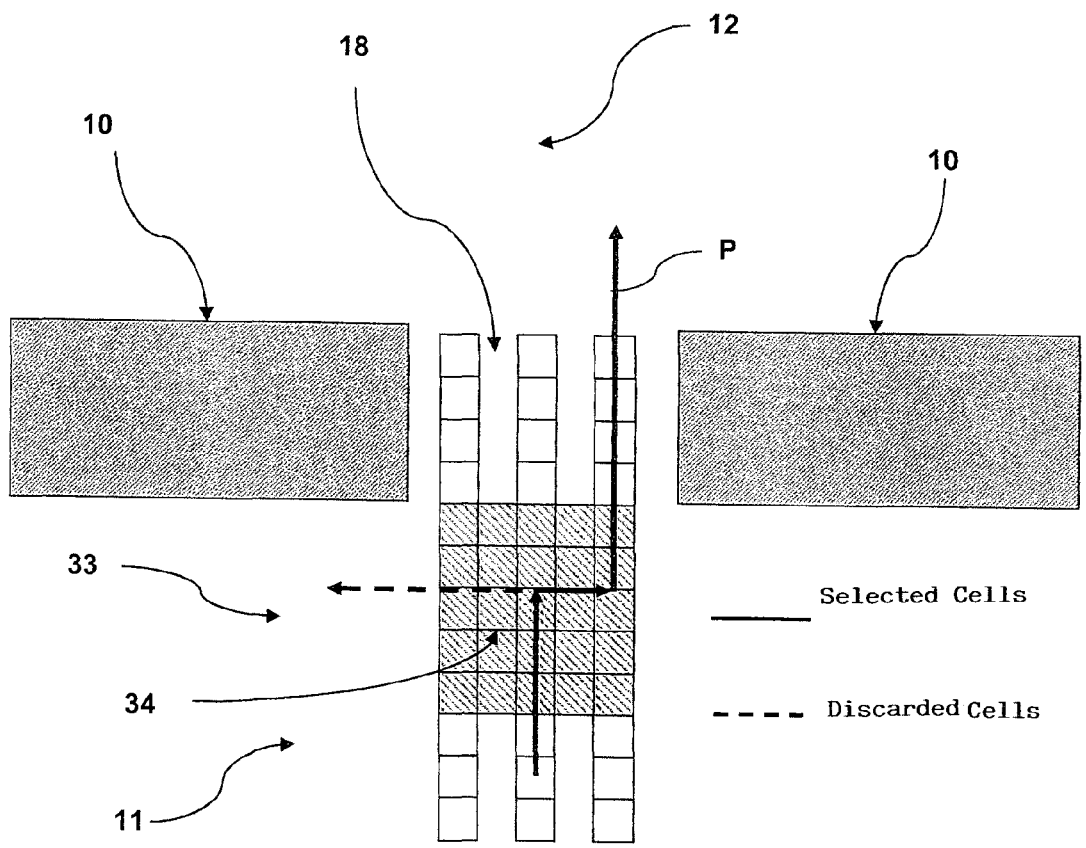
FIG. 10 is a schematic representation of a portion of the device of FIG. 9 which shows a possible embodiment of a phase of discarding/recovery of the particles selected according to the method of the invention.
Figure 11:
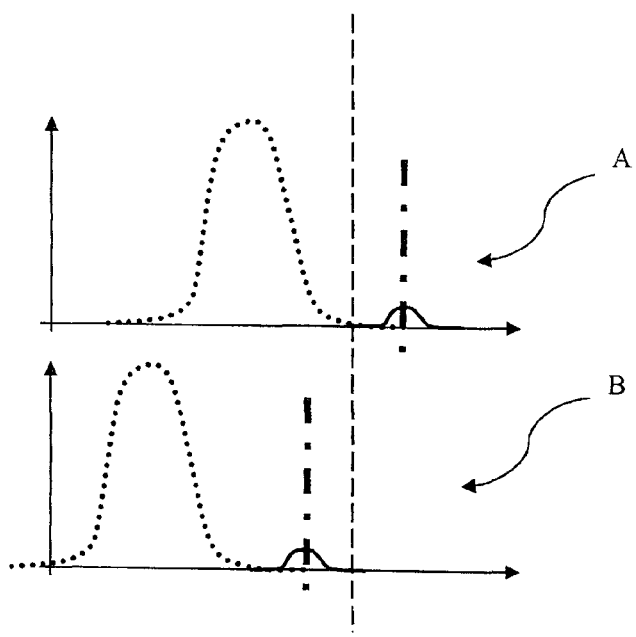
FIG. 11 shows the selection of particles determined within a population of particles as in the known art, using a threshold value determined a priori, i.e. before examination of the entire sample.

As illustrated in FIG. 10, along the path P of the outlet a discard station 33 can be identified comprising an array 34 of selection electrodes which verify, for each particle, whether said particle should be discarded or recovered, according to the result of the outlet control (block 220). If the particle is selected, it goes to the recovery chamber, whereas if it is discarded, it is conveyed to a discard outlet defined in a portion of the loading chamber 11. Said phase of recovery of the particles selected is performed by handling said particles only.

This is followed by the second transfer phase or route-out phase, the aim of which is to convey all the particles selected and confirmed up to that moment to the recovery chamber. From said chamber, the particles can then be recovered and if necessary used for further analysis phases, on external devices or also in situ.

The system used to perform the optimised selection of the particles of interest, once the procedure has been completed, issues a report (block 260) containing the information relative to the analysis just performed.

EXAMPLE 1

Elimination of Clusters

One of the many potential applications of the method according to the present invention is elimination from a particle population of particles grouped to form clusters if their presence is not desired, for example in the case of subsequent use of single particles only. This occurs, for example, in the case of separation of living cells: if the operator wishes to perform a subsequent analysis on single cells, the presence of clusters in the sample could alter acquisition of the data or even the result of the test.

In this case the operator can observe (FIG. 3), via the interface implementing the method according to the invention, the particles and particle clusters that constitute the sample, and identify a plurality of parameters for each of them. In particular, in this case, the radius of the particle or cluster will be measured, in combination with the corresponding coordinates with respect to the surface of the handling device, and a roundness factor of the particle will also be evaluated. Lastly it will be ascertained that the particle is actually located in a site corresponding in use to one of the dielectrophoresis cells used for the handling. To support the selection, the images of the particles or clusters obtained during integral scanning of the sample performed before commencement of the selection operations will also be processed.

Using the cursors relative to a subsequent screenshot of the interface (FIG. 5) in an appropriate manner, the operator selects an upper threshold value for the dimension (radius) of the particles and/or for the roundness, therefore selecting (and then removing them from the device) those in which the data measured exceed said threshold. It should be noted that the index of probability of a cluster is a function of several characteristic parameters of the cell, for example dimension and roundness. In fact, it is highly probable that a large radius measured corresponds not to a single particle with larger dimensions but to a cluster and that a longer shape refers not to a single particle but to several particles grouped in a main direction, i.e. a cluster. If, furthermore, the particles are located at the level of the handling cages of the device, it can be affirmed that the datum measured is relative to particles and not to impurities erroneously present on the surface of the device.

Having appropriately defined threshold values and utility intervals for the quantities examined, the operator selects the clusters present in the sample, checks, if necessary a posteriori, the correctness of his selection and can then remove the clusters from the sample, selectively maintaining inside the handling device the single particles, on which he can perform the analysis at a later stage inside said device.

EXAMPLE 2

Prenatal Diagnosis

For a variety of prenatal diagnosis protocols it is necessary to provide a concentration of a sample of maternal blood, selecting within it the fetal erythrocytes and then performing genetic analysis on them. For said purpose, it is substantially necessary to identify the cells with nucleus, of fetal and not maternal origin. This type of determination can be performed by marking the cells with one or more fluorescent markers, for example a first marker (DAPI) which binds to the nucleus of a cell and a second marker (FITC) which binds selectively to antigens of fetal and not maternal origin. By detecting the fluorescence intensity for the two markers, at two separate respective wavelengths, it is possible to identify the cells for which both markers are present. Since fluorescence detection could be subject to error if cells present phenomena of non-specific autofluorescence—i.e. detectable at any wavelength—it is preferable to perform a third fluorescence detection at a third wavelength (TRITC) so as to determine which cells present said phenomenon and must therefore be excluded, since the detection of fluorescence in the DAPI and FITC channels would not in itself guarantee that the cells are fetal nucleated cells. In this sense, according to the method of the invention, a selection criterion is established for fetal nucleated cells—setting respective values or threshold intervals defined on the basis of processing of a function of the parameters measured and stored—which in effect minimises the possibility of incorrect selections, i.e. the selection of false positives.

Using the interface which implements the method according to the invention, the operator will associate with the coordinates of the particles on the surface of the handling device the value of a plurality of parameters identified during the scan, in addition to the images obtained at the various wavelengths considered, and the value of one or more merit functions calculated on the basis of the parameters identified. In particular (FIGS. 3, 4 and 5), the operator will evaluate the distribution within the cell population of the value of several functions.

A first function is an index of the probability of the cell being a fetal nucleated cell (indicated "fetal" in FIG. 5) and is an index of the fluorescence intensity in the FITC channel developed to compensate for the different illumination in different areas of the chip 8 by the illuminator; a second function (indicated by Dapi in FIG. 5) is an index of the fluorescence intensity in the DAPI channel and is a processed function of the fluorescence intensity; a third function is an index of the probability of the fluorescence detection in the DAPI and FITC channels being actually misleading, since the particle in question presents phenomena of autofluorescence (histogram not named in FIG. 5).

The operator is therefore able to establish, on the basis of observation of the entire sample and in an adaptive manner, intervals of useful values of the fetal function and of the others previously described so as to select only the cells in which the criteria previously discussed have been ascertained.

The invention claimed is:

1. A method for the identification and handling of particles of interest within a population of particles, the method comprising:
    putting the population of particles containing the particles of interest in a microfluidic device;
    scanning the whole microfluidic device and identifying, for each particle of said population of particles in said microfluidic device, at least one parameter from a set of characteristic parameters of said particles of interest;
    selecting from said population of particles in said microfluidic device the particles of interest by comparing for each particle of said population of particles in said microfluidic device said at least one parameter with a respective reference parameter;
    wherein said reference parameter is established on a case by case basis by the steps of:
    storing on a memory device the at least one parameter identified for each particle of said population of particles when scanning the whole microfluidic device;
    determining on a computer device a value of at least one merit function of said at least one stored parameter;
    processing on a computer device the value of said at least one merit function of said at least one stored parameter for each particle of said population of particles;
    displaying the distribution of the value of said merit function within the population of particles on a graphic interface to a user;
    combining said merit function with a selection criterion of said particles of interest, said selection criterion being chosen by the user from a group of possible selection criteria on the basis of the displayed distribution of the value of said merit function within the population of particles; and
    establishing for each particle of said population of particles a threshold criterion to be used as said reference parameter, said threshold criterion being established by the user on a case by case basis based on the combination of the merit function with said chosen selection criterion; and
    separating said particles of interest from the population of particles based on the respective reference parameter, handling only the selected particles of interest.

2. The method of claim 1, wherein said particles are maintained in suspension in a liquid in said microfluidic device.

3. The method of claim 2, wherein said at least one parameter can be detected by at least one sensor located inside or outside said microfluidic device.

4. The method of claim 2, further comprising marking said particles of said population of particles in suspension with at least one specific marker for said particles of interest, said marker being detectable by at least one sensor inside or outside the microfluidic device in which said population of particles has been suspended in said liquid.

5. The method of claim 1, further comprising storing on the memory device a starting position of said particles of interest.

6. The method of claim 5, further comprising:
    moving the particles of interest from their starting position to a respective transfer position; and subsequently storing on the memory device the transfer position for recovery of each particle located in said transfer position.

7. The method of claim 6, wherein each particle located in the transfer position is recovered by handling said particles located in the transfer position only.

8. The method of claim 6, further comprising verifying that the particles of interest selected have been correctly moved from their starting position to the transfer position.

9. The method of claim 1, wherein the said selected particles are separated by capturing each of them in a specific site of a plurality of sites of the microfluidic device.

10. The method of claim 9, wherein said sites are arranged inside said microfluidic device according to an array.

11. The method of claim 9, wherein said microfluidic device is provided with a plurality of different chambers, distinct from, and hydraulically connected to, one another, delimited on at least one face by a base wall of one single chip or by a plurality of separate chips.

12. The method of claim 1, further comprising refining the selection of said particles of interest by displaying on said graphic interface the result of the selection, wherein refining involves all said particles and/or only the particles previously selected and changing the threshold criterion on the basis of the selection result shown on said graphic interface.

13. The method of claim 12, wherein refining comprises controlling each particle selected.

14. The method of claim 13, wherein controlling each particle selected comprises optically displaying on said graphic interface the set of characteristic parameters that can be identified for each particle by means of at least one sensor inside and/or outside said microfluidic device.

15. The method of claim 13 wherein at least one parameter can be detected by means of an external sensor consisting of a camera and controlling each particle selected comprises displaying the images of each particle on said graphic interface.

16. The method of claim 1, further comprising choosing from the group of possible selecting criteria for the particle of interest a criterion that minimizes the possibility of erroneous selections, said choosing involving all said particles and/or only the particles previously selected.

17. The method of claim 1, wherein said at least one parameter is selected in the group consisting of:
a. morphology;
b. optical properties;
c. bio-electric properties;
d. bio-chemical properties;
e. mechanical properties;
f. expression of surface antigens;
g. expression of intra-cytoplasmatic antigens;
h. dielectric properties;
or combinations of the same.

* * * * *